US010765831B1

(12) United States Patent
Skluzacek

(10) Patent No.: US 10,765,831 B1
(45) Date of Patent: Sep. 8, 2020

(54) TRAUMATIC NIGHTMARE DETECTION AND INTERVENTION

(71) Applicant: NightWare, Inc., Minneapolis, MN (US)

(72) Inventor: Tyler Skluzacek, Chicago, IL (US)

(73) Assignee: NIGHTWARE, INC., Minneapolis, MN (US)

( * ) Notice: Subject to any disclaimer, the term of this patent is extended or adjusted under 35 U.S.C. 154(b) by 133 days.

(21) Appl. No.: 15/713,313

(22) Filed: Sep. 22, 2017

Related U.S. Application Data

(60) Provisional application No. 62/398,908, filed on Sep. 23, 2016.

(51) Int. Cl.
| | |
|---|---|
| *A61M 21/02* | (2006.01) |
| *A61B 5/00* | (2006.01) |
| *A61B 5/0205* | (2006.01) |
| *A61B 5/16* | (2006.01) |
| *A61B 5/11* | (2006.01) |
| *A61M 21/00* | (2006.01) |
| *A61B 5/024* | (2006.01) |

(52) U.S. Cl.
CPC ........... *A61M 21/02* (2013.01); *A61B 5/0205* (2013.01); *A61B 5/165* (2013.01); *A61B 5/4815* (2013.01); *A61B 5/4836* (2013.01); *A61B 5/681* (2013.01); *A61B 5/024* (2013.01); *A61B 5/11* (2013.01); *A61B 2562/0219* (2013.01); *A61M 2021/0022* (2013.01); *A61M 2021/0027* (2013.01); *A61M 2021/0044* (2013.01); *A61M 2205/3303* (2013.01); *A61M 2230/06* (2013.01); *A61M 2230/63* (2013.01)

(58) Field of Classification Search
CPC ..................................................... A61M 21/02
USPC ......................................................... 434/236
See application file for complete search history.

(56) References Cited

U.S. PATENT DOCUMENTS

| | | | |
|---|---|---|---|
| 2014/0245784 A1* | 9/2014 | Proud | A44C 5/0015 63/1.11 |
| 2015/0031964 A1* | 1/2015 | Bly | A61B 5/7465 600/301 |
| 2015/0169844 A1* | 6/2015 | Munafo | G06F 19/3481 705/2 |
| 2016/0296157 A1* | 10/2016 | Girouard | A61B 5/4094 |

* cited by examiner

*Primary Examiner* — Kesha Frisby
(74) *Attorney, Agent, or Firm* — Schwegman Lundberg & Woessner, P.A.

(57) ABSTRACT

The present disclosure, in one embodiment, is a computer-implemented method for the detection of and intervention in traumatic nightmares. In one embodiment, a user wears a watch wirelessly connected to a phone. The watch may include an accelerometer, gyroscope, and heartrate monitor. The application may monitor these sensors and intervene with haptic feedback if the application detects a traumatic nightmare. In one embodiment, the application may include a monitoring module that collects data from the watch's accelerometer, gyroscope, and heartrate sensors. The application may then estimate and record stress levels based on these sensors. The application may also include an intervention module that responds to high stress levels with haptic feedback that increases in intensity of previous efforts to intervene were unsuccessful.

18 Claims, 6 Drawing Sheets

100 102 104 106 108

TRAUMATIC NIGHTMARE DETECTION AND INTERVENTION

CROSS-REFERENCE TO RELATED APPLICATIONS

This application claims the benefit of provisional patent application 62/398,908, filed Sep. 23, 2016 by the present inventor.

BACKGROUND OF THE INVENTION

Field of the Invention

The present disclosure relates to nightmares, particularly the detection of and intervention in traumatic nightmares.

Discussion of the Background

The background description provided herein is for generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Nightmares are a condition that affects a substantial number of persons, particularly concerning segments of the population that experience nightmares are adults who have post-traumatic stress disorder (PTSD). Military veterans, first responders, and crime victims may be particularly afflicted with nightmares because of traumatic experiences that have created PTSD. Traumatic nightmares can be so impactful that restful sleep is negatively affected, and fragmented, possibly at times rendering people unable to function normally in their daily lives.

Many researchers have attempted to solve for traumatic nightmares, generally involving complex solutions in clinical settings using prolonged exposure or similar treatments. Drawbacks to existing solutions include cost, complexity, side effects, and inability to eliminate the effects of nightmares.

Problems associated with PTSD are particularly acute in the community of military veterans who have returned from combat operations, where the effort needed to begin clinical treatment may be great. Moreover, issues of self-esteem with military veterans may prevent them from pursuing clinical treatment, thereby prolonging their condition.

A method that uses readily available and relatively low-cost technology to monitor the sleep cycle of a person who experiences nightmares to interrupt the sleep cycle sufficiently to prevent the full onset of the nightmare from occurring, would provide decided advantages.

BRIEF SUMMARY OF THE INVENTION

The following presents a simplified summary of one or more embodiments of the present disclosure to provide a basic understanding of such embodiments. This summary is not an extensive overview of all contemplated embodiments, and is intended to neither identify key or critical elements of all embodiments, nor delineate the scope of any or all embodiments.

The present disclosure, in one embodiment, is a computer-implemented method for the detection of and intervention in traumatic nightmares. In one embodiment, a user wears a watch wirelessly connected to a phone. The watch may include an accelerometer, gyroscope, and heartrate monitor. The application may monitor these sensors and intervene with haptic feedback if the application detects a traumatic nightmare.

In one embodiment, the application may include a monitoring module. A user may tap the applications' start button to begin monitoring. The application may spend the next minute collecting data from the watch's accelerometer, gyroscope, and heartrate sensors. The application may average the sensor values over the previous minute. The application may compute an instantaneous stress magnitude for the previous minute. The application may compute an average stress magnitude by averaging the instantaneous stress magnitudes over the last five minutes. The application may record the average sensor values, instantaneous stress magnitude, and average stress magnitude locally and in the cloud.

In one embodiment, the application may include an intervention module. The module may receive a notification that the application recorded a sample. The module may determine whether it has collected at least 4,000 samples. If so, the module may determine if the module has intervened in the last five minutes. If not, the module may use the last 4,000 average stress magnitudes to compute a $90^{th}$ percentile average stress magnitude. The module may then determine if the current average stress magnitude exceeds the $90^{th}$ percentile average stress magnitude. If so, the module may intervene with an appropriate intensity based on the effectiveness of recent interventions.

BRIEF DESCRIPTION OF THE SEVERAL VIEWS OF THE DRAWING

While the specification concludes with claims particularly pointing out and distinctly claiming the subject matter that is regarded as forming the various embodiments of the present disclosure, it is believed that the invention will be better understood from the following description taken in conjunction with the accompanying figures:

DETAILED DESCRIPTION OF THE INVENTION

Figure 1:
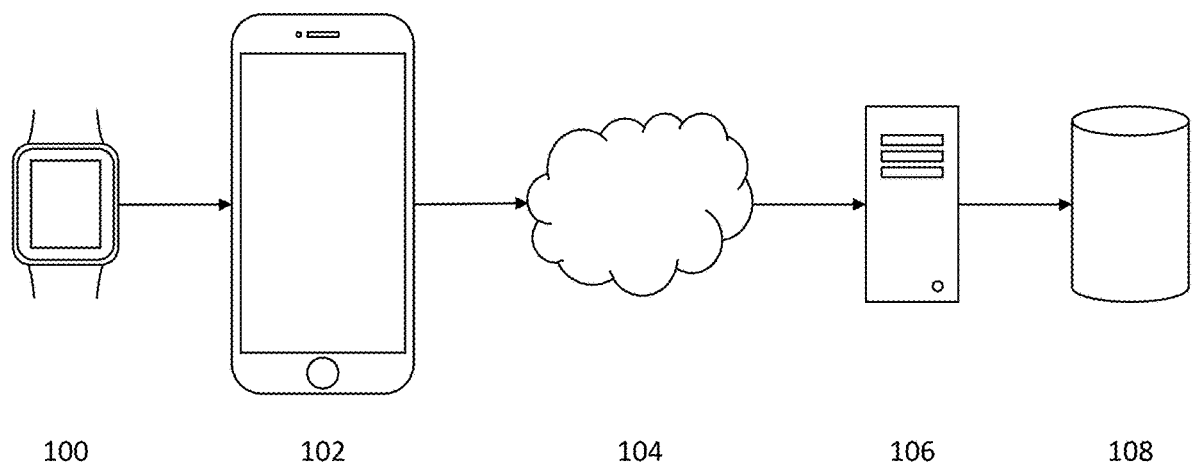
FIG. 1: System Diagram

FIG. 1 is a system diagram illustrating an embodiment of the present disclosure. In it, a watch 100 may connect to a phone 102 via Bluetooth or some other means. The phone 102 may connect via a network 104 to a sever 106. The server 106 may connect to a database 108. The database 108 may contain data collected by the watch 100 and/or phone 102. One skilled in the art will recognize that many other system configurations are possible. For example, instead of running an application on a phone 102 that communicates with a watch 100, one might omit the phone 102 and run the application directly on the watch 100. Also, one might omit the network 102, server 106, and database 108 and run in an offline mode. In addition, one might replace the watch 100 with a variety of other devices capable of monitoring a person during sleep and/or intervening in the event of a nightmare. For example, one might replace with watch with an armband, headband, chest band, bed monitor, patch, etc. To intervene in the event of a nightmare, one might use haptic feedback, lights, sound, etc. In addition, one might combine these devices in a variety of ways.

Figure 2:
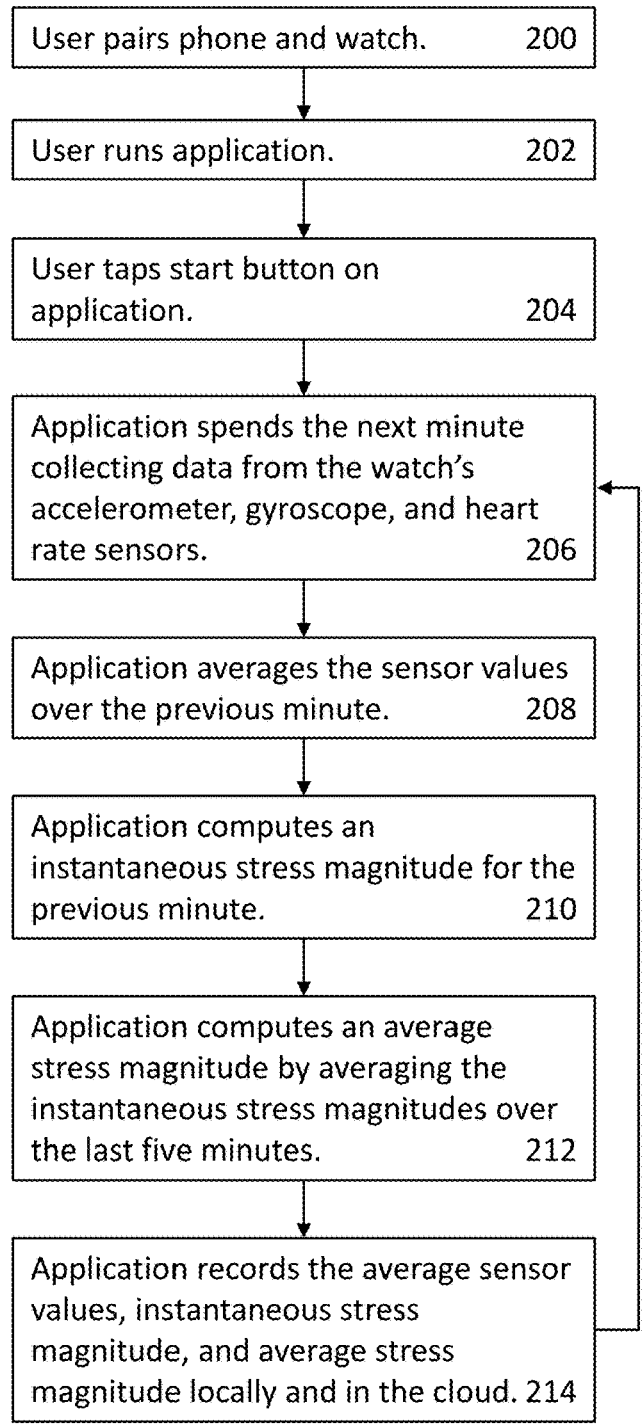
FIG. 2: Monitor Flowchart

FIG. 2 is a monitor flowchart of an embodiment of the present disclosure. In it, a user may begin at step 200 by pairing a phone 102 and watch 100. At step 202, the user may run the application on the phone 102. At step 204, the user may tap a start button in the application. At step 206, the application may spend the next minute collecting data from the watch's accelerometer, gyroscope, and heartrate sensors. At step 208, the application may average the sensor values over the previous minute. At step 210, the application may compute an instantaneous stress magnitude for the previous minute. To do this, one might use the following equations:

$$g = \sqrt{g_x^2 + g_y^2 + g_z^2}$$

$$s = \frac{\sqrt{0.125a^2 + 0.125g^2 + h^2}}{1.6125}$$

The first equation may enable one to compute a gyroscope magnitude from the gyroscope's components. The second equation may enable one to calculate a stress magnitude from accelerometer, gyroscope, and heart rate values. For example, let's say we have an average accelerometer value of 51 meters per second squared, average gyroscope values of (x=40, y=20, and z=185) radians per second, and an average heartrate of 75 beats per minute. The first equation gives us a gyroscope magnitude of approximately 190 radians per second. The second equation gives us a stress magnitude of approximately 63.

$$g = \sqrt{40^2 + 20^2 + 185^2} \approx 190$$

$$s = \frac{\sqrt{0.125(51)^2 + 0.125(190)^2 + (75)^2}}{1.6125} \approx 63$$

At step 212, the application may compute an average stress magnitude by averaging the instantaneous stress magnitudes over the last five minutes. At step 214, the application may record the average sensor values, instantaneous stress magnitude, and average stress magnitude locally and in the cloud.

One skilled in the art will recognized that one could use a variety of sensors to monitor a user including accelerometers, galvanic skin response sensors, gyroscopes, heartrate sensors, oximetry sensors, microphones, temperature sensors, etc.

One skilled in the art will also recognize that one could detect not just traumatic nightmares, but also other events such as daytime anxiety episodes, flashbacks, etc. Also, one might detect not just the event, but precursors thereof.

Figure 3:
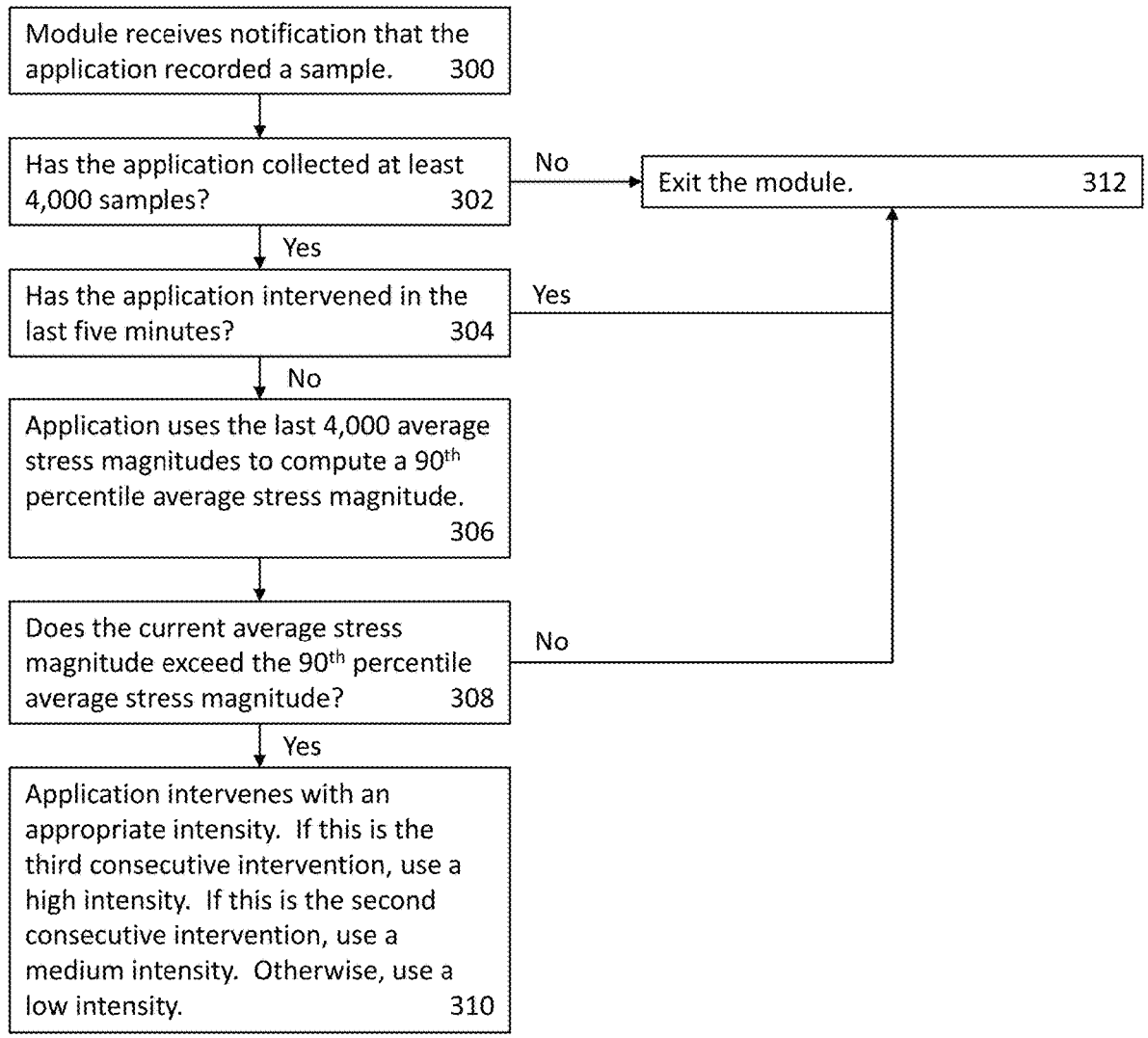
FIG. 3: Intervention Flowchart

FIG. 3 is an intervention flowchart of an embodiment of the present disclosure. At step 300, the module may receive a notification that the application recorded a sample. At step 302, the module may determine whether it has collected at least 4,000 samples. If not, the module may advance to step 312 and exit. If so, the module may advance to step 304 and determine if the module has intervened in the last five minutes. If so, the module may advance to step 312 and exit. If not, the module may advance to step 306 and use the last 4,000 average stress magnitudes to compute a $90^{th}$ percentile average stress magnitude. At step 308, the module may determine if the current average stress magnitude exceeds the $90^{th}$ percentile average stress magnitude. If not, the module may advance to step 312 and exit. If so, the module may advance to step 310 and intervene with an appropriate intensity. If this is the third consecutive intervention, the module may use a high intensity. If this is the second consecutive intervention, the module may use a medium intensity. Otherwise, the module may use a low intensity. One embodiment of the present disclosure uses the following vibration patterns for these intensities. For each pattern, the first number is a duration in millisecond without vibration, the second number is a duration in millisecond with vibration, the third number is a duration in milliseconds without vibration, etc.

Low=0, 150, 100, 150, 500, 150, 100, 150, 500, 150, 100, 150

Medium=0, 250, 100, 250, 500, 250, 100, 250, 500, 250, 100, 250

High=0, 350, 100, 350, 500, 350, 100, 350, 500, 350, 100, 350

In one embodiment of the disclosure, the low intensity intervention may be to arouse, but not awaken. Higher intensity interventions may result in more significant responses including waking the user.

One skilled in the art will recognize that many other equations may be suitable for detecting and responding to a stressful event. One could use different sensors and different equations to detect a stressful event. One could have different training procedures and durations. One could use any number of samples during training. One could use a different percentile to detect a traumatic event or use a different technique to detect these events. One could average results over longer or shorter periods of time. One could use a variety of techniques to intervene (e.g. light or sound). One could use different vibration patterns. One could have any number of different intensity levels. One could have different rules dictating when to intervene. Also, one could easily omit the steps of starting and stopping the monitoring (e.g. there are many techniques to detect sleep states based on biometric indicators).

One skilled in the art will recognize that the application could respond to a detected event in a variety of ways including contacting someone (e.g. via e-mail, phone, or text), scheduling an appointment (e.g. with a doctor or psychiatrist), etc.

One skilled in the art will also recognize that one could simply monitor an individual and not intervene. This may be useful in a variety of settings where one is trying different approaches to address traumatic nightmares and using an embodiment of the present disclosure to see what impact those approaches are having on the individual as he or she sleeps.

Figure 4:
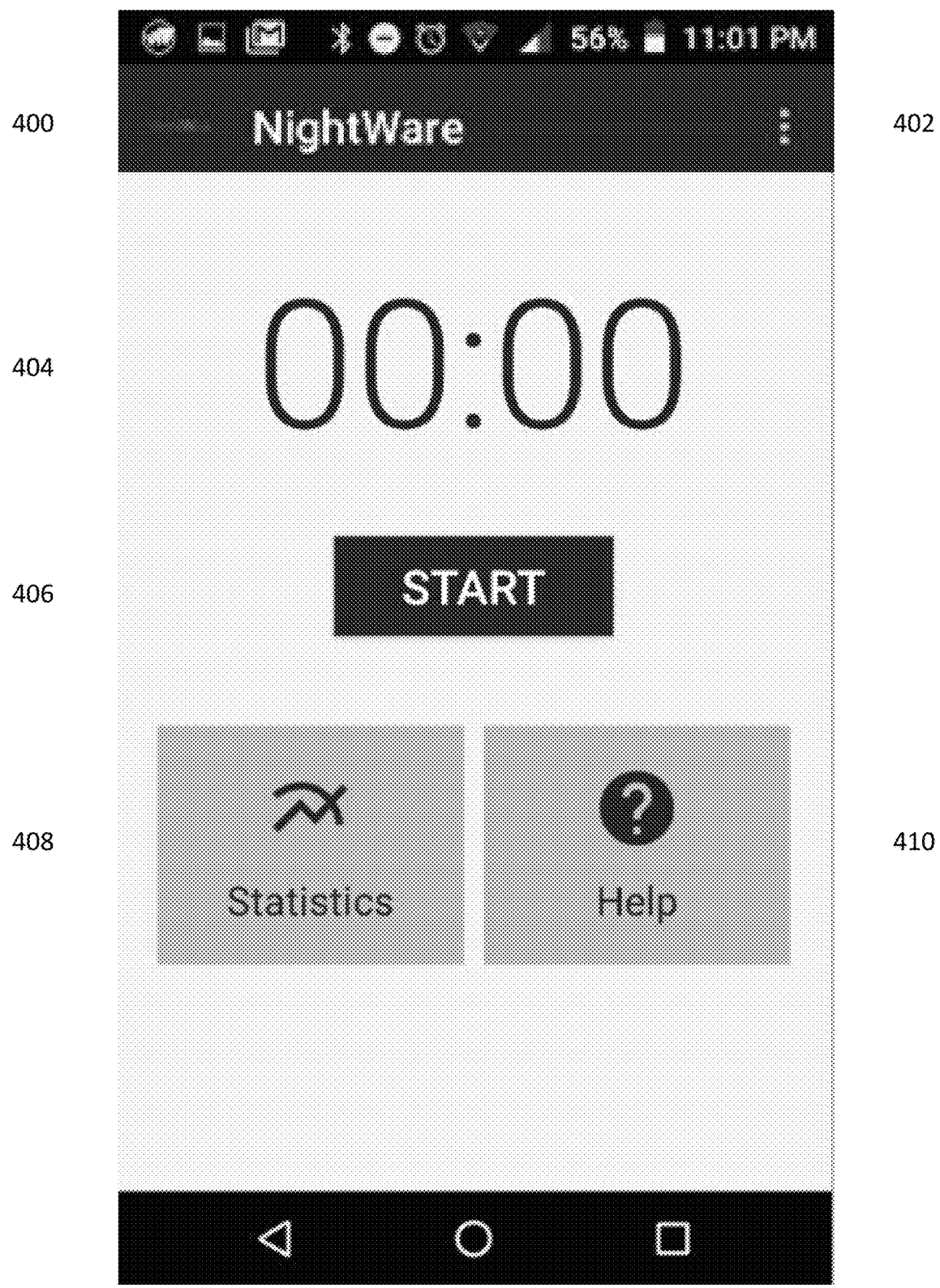
FIG. 4: Start Screen

FIG. 4 is a start screen in an embodiment of the present disclosure. The start screen may enable a user to start monitoring before going to bed. The start screen may include a title 400, menu 402, duration 404, start button 406, statistics button 408, and help button 410. When a user taps the start button 406, the application may show a stop screen (FIG. 5), start monitoring, and start updating the duration 404. When the user taps the statistics button 408, the application may display a statistics screen (FIG. 6).

Figure 5:
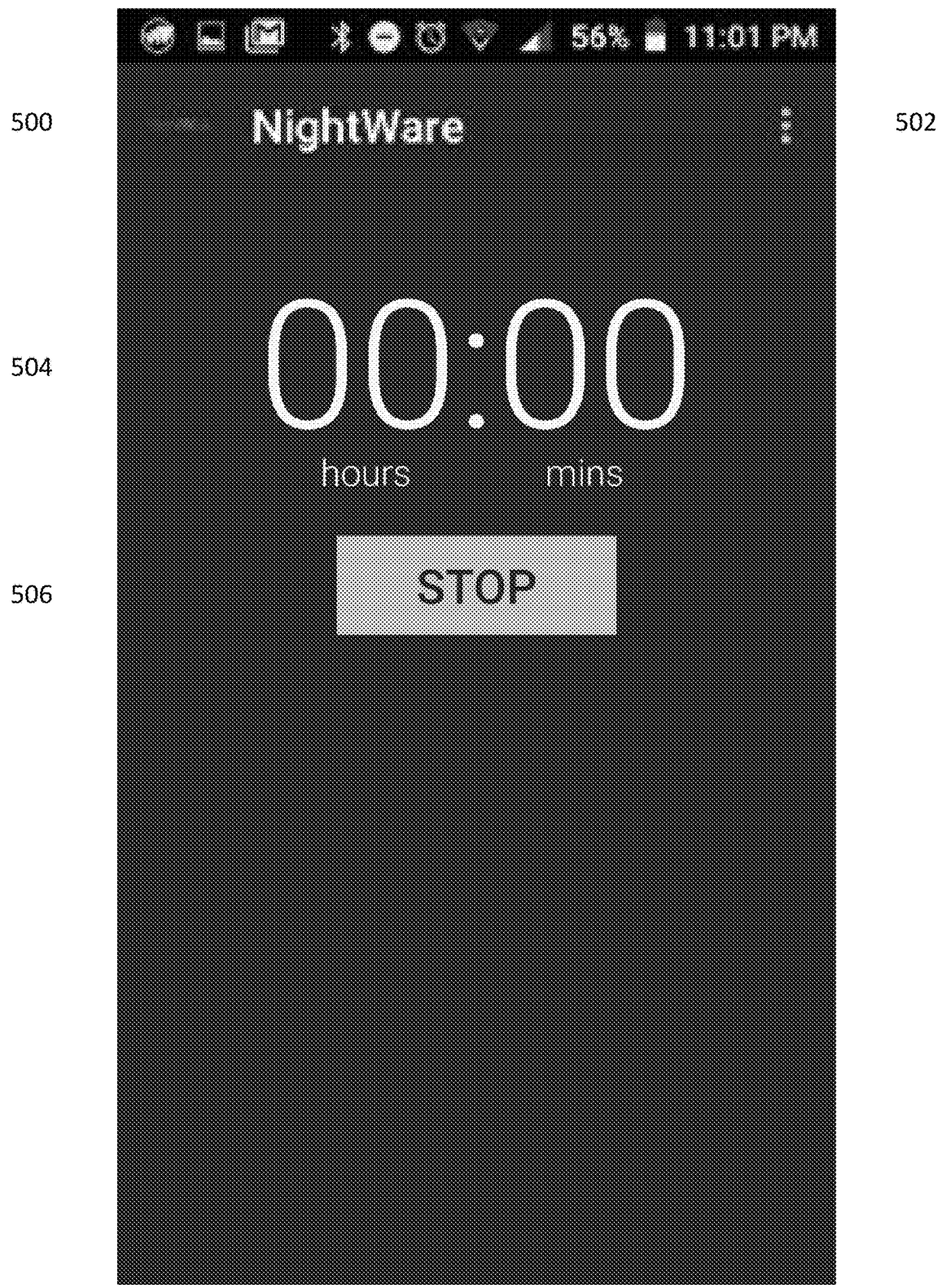
FIG. 5: Stop Screen

FIG. 5 is a stop screen in an embodiment of the present disclosure. The stop screen may enable a user to stop monitoring after waking up. The stop screen may include a title 500, menu 502, duration 504, and stop button 506. When the user taps the stop button 506, the application may show a start screen (FIG. 4), stop monitoring, and stop updating the duration 504.

Figure 6:
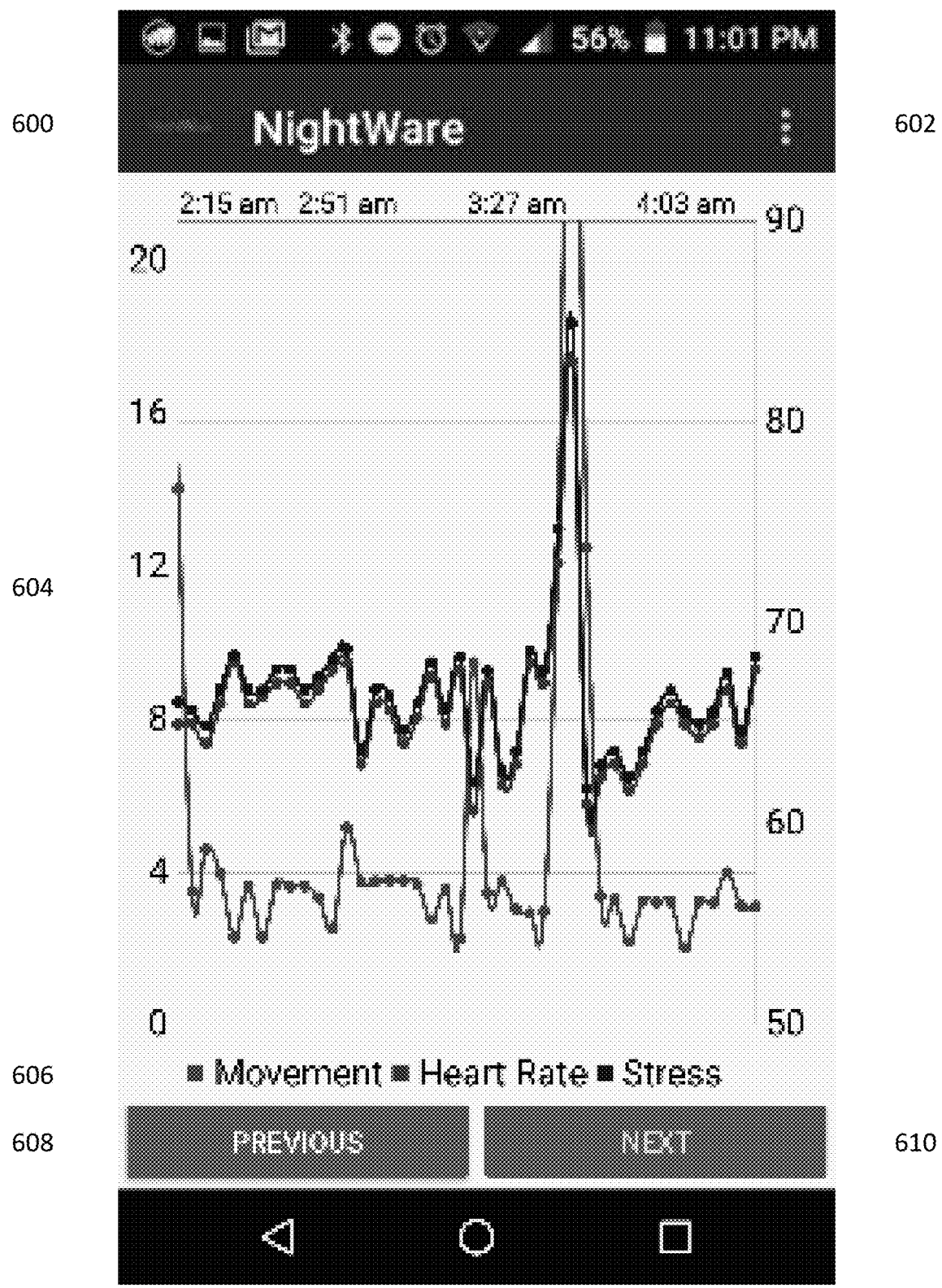
FIG. 6: Statistics Screen

FIG. 6 is a statistics screen in an embodiment of the present disclosure. The statistics screen may enable a user to review heartrate, movement, stress levels during previous nights. The statistics screen may include a title 600, menu 602, chart 604, key 606, previous button 608, and next button 610. The chart 604 may show heartrate, movement, stress levels over time. Tapping the previous button 608 may go back in time and tapping the next button 610 may go forward in time.

I claim:

1. A method of detecting and intervening in traumatic nightmares, the method comprising:
monitoring a user by collecting data from at least two of an accelerometer, a gyroscope, or a heartrate sensor of at least one device worn by the user;
determining average values for each of the at least two of the accelerometer, gyroscope, or heartrate sensor over a first period of time and detecting traumatic nightmares or precursors thereof based on a combination of the average values; and
causing an intervention based upon detection of a traumatic nightmare or precursor thereof;
wherein detecting traumatic nightmares or precursors thereof based on a combination of the average values comprises averaging combinations of the average values over a second period of time greater than the first period of time; and
wherein average values for each of the at least two of the accelerometer, gyroscope, or heartrate sensor are determined over a plurality of first periods of time, and the average values corresponding to the plurality of first periods of time are averaged over the second period of time.

2. The method of claim 1, wherein the at least one device worn by the user comprises a watch, armband, or chest band.

3. The method of claim 1, wherein the combination of the average values corresponds to an estimate of stress of the user.

4. The method of claim 1, wherein the plurality of first periods of time are each about one minute, and the second period of time is about five minutes.

5. The method of claim 1, wherein monitoring a user by collecting data comprises collecting data from each of an accelerometer, a gyroscope, and a heartrate sensor.

6. The method of claim 5, wherein the combination of the average values comprises a stress magnitude value calculated using an equation:

$$s = \frac{\sqrt{0.125a^2 + 0.125g^2 + h^2}}{1.6125}$$

wherein s is the stress magnitude value, a is the average value of the accelerometer over the first period of time, g is the average value of the gyroscope over the first period of time, and h is the average value of the heartrate sensor over the first period of time.

7. A method of detecting traumatic nightmares, the method comprising:
monitoring a user by collecting data from at least two of an accelerometer, a gyroscope, or a heartrate sensor of at least one device worn by the user; and
determining average values for each of the at least two of the accelerometer, gyroscope, or heartrate sensor over a first period of time and detecting traumatic nightmares or precursors thereof based on a combination of the average values;
wherein detecting traumatic nightmares or precursors thereof based on a combination of the average values comprises averaging combinations of the average values over a second period of time greater than the first period of time.

8. The method of claim 7, wherein monitoring a user by collecting data comprises collecting data from each of an accelerometer, a gyroscope, and a heartrate sensor.

9. The method of claim 8, wherein the combination of the average values comprises a stress magnitude value calculated using an equation:

$$s = \frac{\sqrt{0.125a^2 + 0.125g^2 + h^2}}{1.6125}$$

wherein s is the stress magnitude value, a is the average value of the accelerometer over the first period of time, g is the average value of the gyroscope over the first period of time, and h is the average value of the heartrate sensor over the first period of time.

10. The method of claim 7, wherein average values for each of the at least two of the accelerometer, gyroscope, and heartrate sensor are determined over a plurality of first periods of time, and the average values corresponding to the plurality of first periods of time are averaged over the second period of time.

11. The method of claim 7, further comprising causing an intervention based upon detection of a traumatic nightmare or precursor thereof.

12. The method of claim 11, wherein the combination of the average values corresponds to an estimate of stress of the user.

13. The method of claim 12, wherein the estimate of stress is compared to a plurality of prior stress estimates for the user, and wherein causing an intervention comprises causing an intervention if the estimate of stress is above a specified percentile of the prior stress estimates.

14. A method of detecting and intervening in traumatic nightmares, the method comprising:
monitoring a user by collecting data from at least two of an accelerometer, a gyroscope, or a heartrate sensor of at least one device worn by the user;
determining average values for each of the at least two of the accelerometer, gyroscope, or heartrate sensor over a first period of time and detecting traumatic nightmares or precursors thereof based on a combination of the average values;
detecting a plurality of traumatic nightmares or precursors thereof of the user over a second period of time; and
causing an intervention based upon detection of a traumatic nightmare or precursor thereof, wherein causing an intervention comprises causing at least one of vibration, light, or sound from the at least one device worn by the user.

15. The method of claim 14, wherein the at least one of vibration, light, or sound increases in intensity between at least two of the plurality of traumatic nightmares or precursors thereof of the user detected over the second period of time.

16. The method of claim 15, wherein a first intensity of the at least one of vibration, light, or sound is configured to arouse, but not awaken, the user.

17. The method of claim 16, wherein at least one other intensity of the at least one of vibration, light, or sound is configured to awaken the user.

18. The method of claim 14, wherein there is a minimum duration between interventions.

* * * * *